United States Patent [19]
Emil

[11] 3,987,788
[45] Oct. 26, 1976

[54] SYSTEM FOR COMPUTING CARDIAC FLOW RATES FROM THERMODILUTION MEASUREMENTS

[75] Inventor: Tuncay Emil, Fountain Valley, Calif.

[73] Assignee: American Hospital Supply Corporation, Evanston, Ill.

[22] Filed: July 9, 1975

[21] Appl. No.: 594,210

[52] U.S. Cl. .............................. 128/2.05 F; 73/204
[51] Int. Cl.² ........................................... A61B 5/02
[58] Field of Search.................. 128/2.05 F, 2.05 R, 128/2.05 V, 2 R; 73/204

[56] References Cited
UNITED STATES PATENTS

| | | | |
|---|---|---|---|
| 3,269,386 | 8/1966 | Sherman......................... | 128/2.05 F |
| 3,651,318 | 3/1972 | Czekajewski............... | 128/2.05 F X |
| 3,678,922 | 7/1972 | Philips et al..................... | 128/2.05 F |

OTHER PUBLICATIONS

*Journ. of Assoc. for Advancement of Medical Instr.*, vol. 6, No. 2, Mar.–Apr. 1972, pp. 116–121.

*Primary Examiner*—Kyle L. Howell
*Attorney, Agent, or Firm*—Dawson, Tilton, Fallon & Lungmus

[57] ABSTRACT

A thermistor is used to sense the temperature of blood at a location downstream of a point at which a small quantity of liquid (indicator) having a temperature lower than the blood is introduced. Circuitry is used to compute the flow measurement from the sensed blood temperature according to the Stewart-Hamilton dilution equation for a thermal indicator. Values are manually entered into the system for a computation constant, the temperature of the body and the temperature of the indicator. The thermodilution curve sensed by the thermistor is integrated through the peak value to a predetermined per cent of the peak value and increased by a predetermined per cent to generate an estimated integral value. The flow value is computed in a dual slope ratiometric analog-to-digital converter by taking the ratio of the product of the temperature difference times the computation constant to the estimated integral value.

12 Claims, 9 Drawing Figures

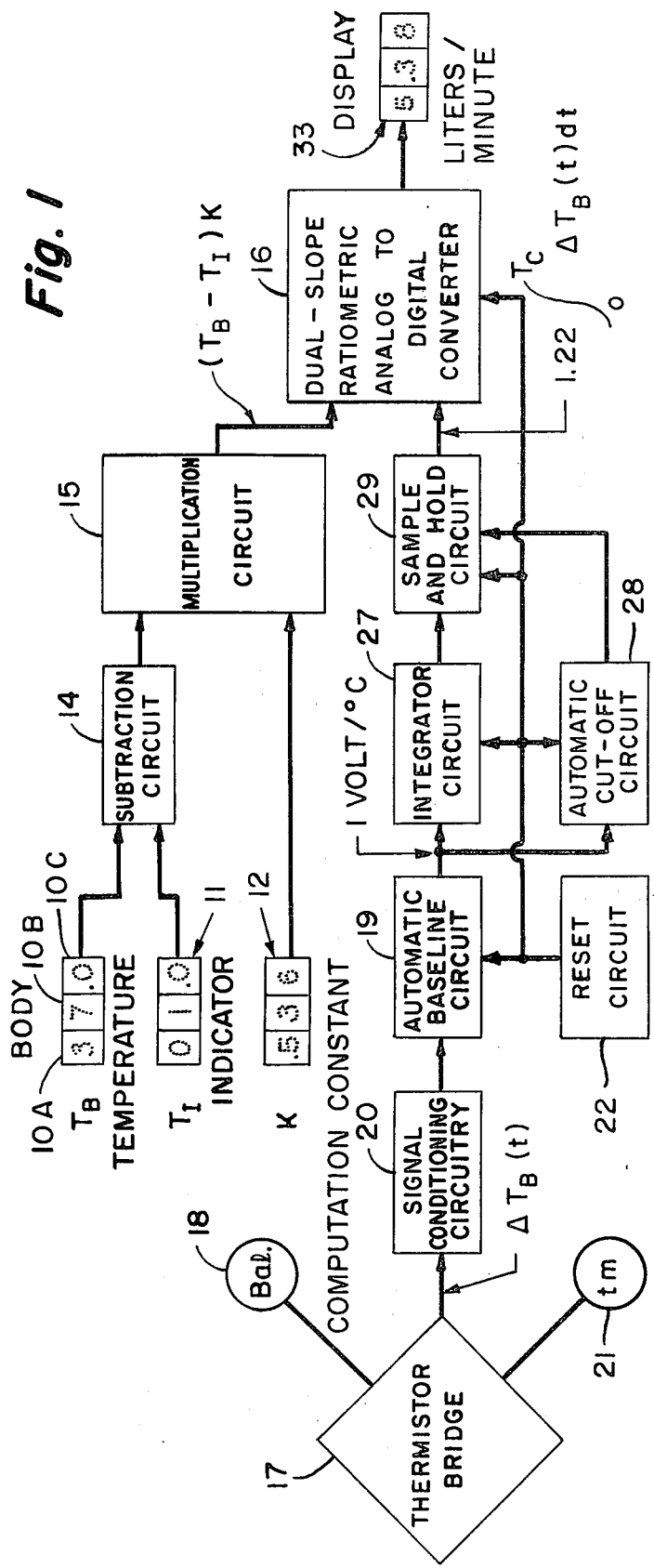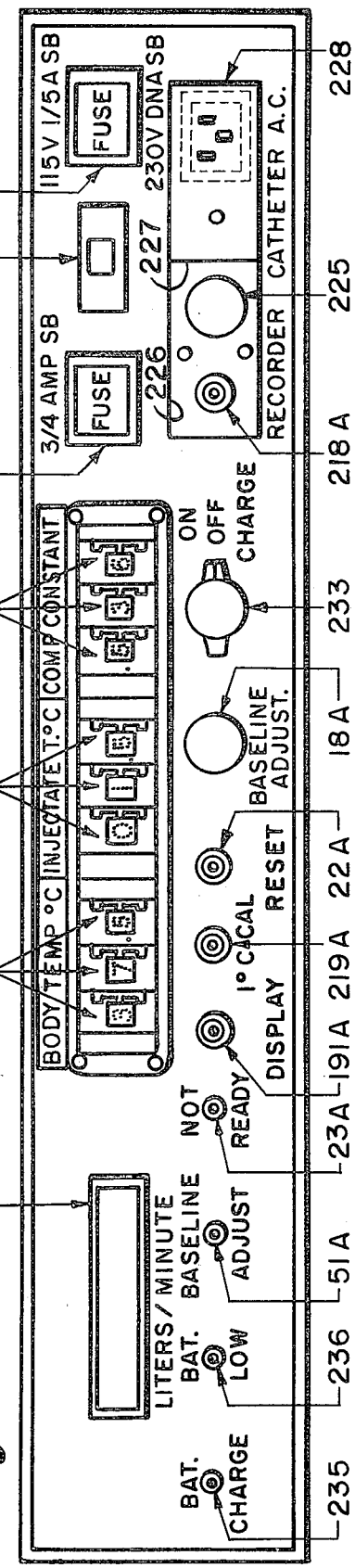

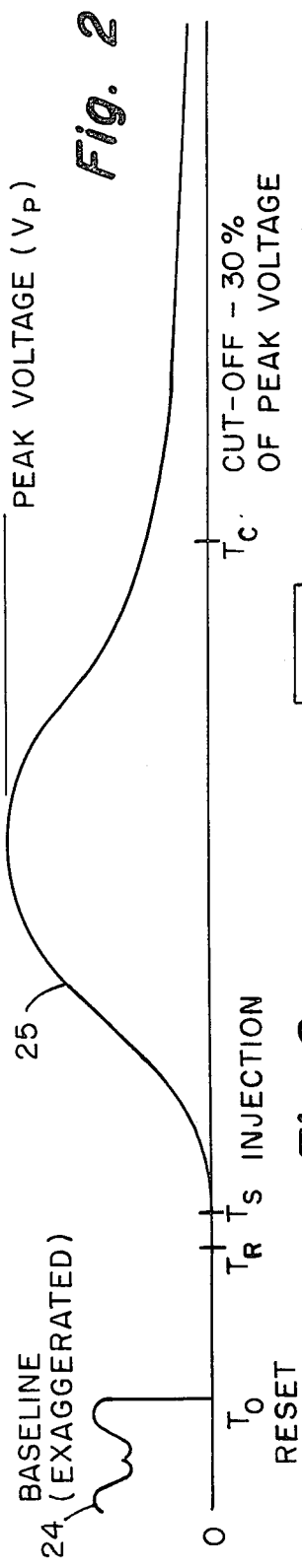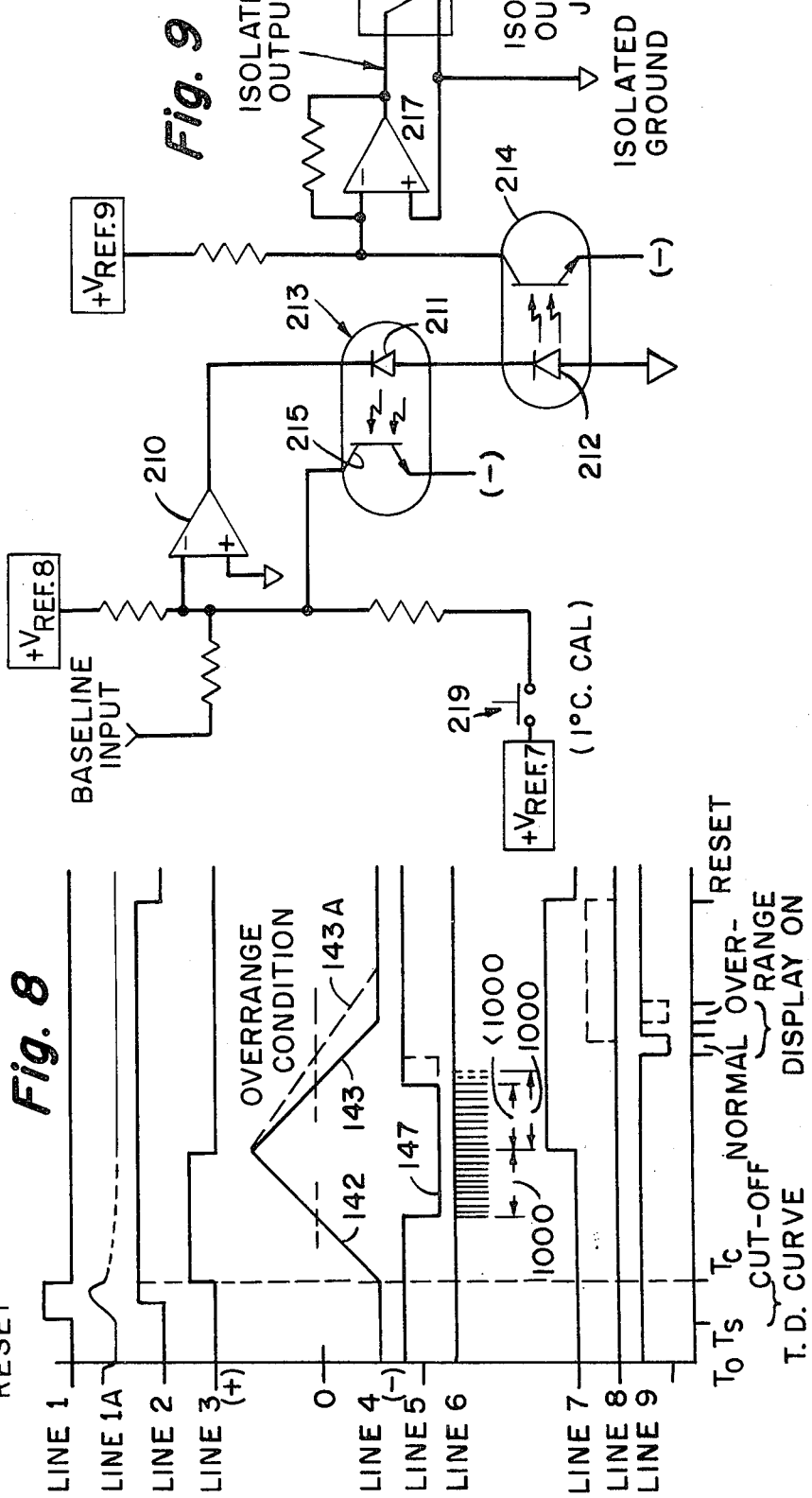

SYSTEM FOR COMPUTING CARDIAC FLOW RATES FROM THERMODILUTION MEASUREMENTS

BACKGROUND AND SUMMARY

The present invention relates to a system or instrument for computing blood flow rates for vascular systems. In particular, the present invention employs what is referred to in the art as "thermodilution" techniques.

The principle upon which the thermodilution technique is based is that the change of heat of a substance is related to its mass and specific heat for a given change in temperature. For a static system, if two substances at different temperatures are mixed, the resulting temperature of the mixture will fall between the starting temperatures of the two substances. If the mass of one substance is unknown, it can be determined by equating at equilibrium the change in heat of the two substances and calculating the unknown mass from the resulting equation.

When this principle is applied to a system of continuous flow, as in the heart and vasculature, a small amount of relatively cool substance (called the "indicator") is introduced into and mixed with the flowing substance (i.e., the blood), thereby yielding a time-temperature curve which may be sensed slightly downstream of the point at which the indicator is introduced into the system. This curve is referred to as the "thermodilution curve", and the area under the thermodilution curve represents the sum of the instantaneous mixed temperatures at the sensing point. The well-known Stewart-Hamilton equation relates the unknown flow of mass per unit time to the change of heat in the mixture, the specific heat, and the change in temperature.

It is desired that the amount of the indicator introduced into the bloodstream is small relative to the mass of body tissue (including blood).

The thermodilution technique for determining cardiac output flow utilizes the Stewart-Hamilton indicator dilution equation as modified for a thermal indicator, as follows:

$$C.O. = \frac{(1.08) \, C_T \, (60) \, V_I \, (T_B - T_I)}{\int_0^\infty \Delta T_B(t) \, dt} \quad (1)$$

Where:

| | | |
|---|---|---|
| C.O. | = | Cardiac output in Liters/Minute |
| $1.08 = \frac{\rho C_p \, (5\% \text{ Dextrose})}{\rho C_p (\text{Blood})}$ | | This is the ratio of the density times the specific heat of 5 % Dextrose to the density times the specific heat of blood. |
| $C_T$ | = | Correction factor for the injectate temperature rise through the catheter |
| 60 | = | Seconds/Minute |
| $V_I$ | = | Volume of injectate in liters |
| $T_B$ | = | Initial blood temperature in °C |
| $T_I$ | = | Initial injectate temperature in °C |
| $\int_0^\infty \Delta T_B(t) \, dt =$ | | Area under the thermodilution curve in °C-Sec. |

The first four terms of Equation (1), namely [(1.08 $C_T$) 60 $V_I$] are grouped together and entered into the system of the present invention as a preset constant value, called the "computation constant". The temperature of the blood, $T_B$, and the initial temperature of the indicator or injectate, $T_I$, are separately entered in a similar manner. All of the entries of constants are made prior to initiating the test—that is, prior to generating the thermodilution curve.

The present system determines the difference between $T_B$ and $T_I$ and multiplies this difference by the computation constant. The resulting value, sometimes referred to as the "numerator value" of the equation is internally stored for later processing. To conduct a test, a catheter is inserted into the pulmonary artery. The catheter also contains a port spaced from the thermistor for introducing a known amount of indicator at a predetermined temperature. A sensing thermistor is located on the catheter, and the catheter is inserted in such a manner that the sensor is located downstream in the direction of blood flow from the point of injection of the indicator. Hence, the thermistor senses the temperature of the blood at a location downstream of the point of injection of the indicator, and generates a time-temperature thermodilution signal which is then amplified and integrated. Integration of the thermodilution signal is terminated after the curve has peaked and begins to diminish to a predetermined value equal to 30% of its peak value. The total integral is then estimated by increasing the value of the truncated integral by a fixed percentage. Studies have shown that if the integration is carried out until the curve returns to 30% of its peak value, then the truncated integral value must be increased by 22% to estimate the remaining portion of "tail" of the integral. The resulting value is sometimes referred to as the "estimated integral value". The amount by which the truncated integral value is increased to determine the estimated integral value is, of course, dependent upon the point at which the integration terminates. As mentioned, in the preferred embodiment, where the integration is carried out to a point at which the thermodilution curve returns to a value equal to 30% of its peak value, then the value of the truncated integral must be enhanced by 22%. The increase of the truncated integral value may be accomplished either by increasing the gain of an amplifier to be 1.22 greater than unity gain, or there may be a separate computation of 22% of the truncated integral value which would then be added to the truncated integral value.

Statistical analysis of over 200 thermodilution procedures indicates that measurement error is minimized if the integration is terminated when the curve returns to 30% of its peak value. The ratio of the numerator value stored in the system and described above to the estimated integral value is then computed in a dual-slope ratiometric analog-to-digital converter to compute the final value of cardiac output flow.

Systems are known for computing cardiac flow rates, such as those discussed and the one claimed in U.S. Pat. No. 3,678,922, granted July 25, 1972, to Philips et al. In the latter system, integration of a dilution curve is terminated at a cutoff point which is defined in terms of the peak of the response signal. The cutoff point of the response signal is determined to compensate for error normally introduced due to recirculation of the indicator. Recirculation occurs when the indicator passes the sensor a second time so as to obscure the true reading of the integral of the thermodilution curve. Although recirculation may cause measurement errors for a dye dilution procedure, (since the effect of the dye is not readily diminished), no substantial recirculation problems have been experienced in the case of thermodilution measurements. Nevertheless, it is desirable to terminate integration of the thermodilution curve before the curve approaches the baseline to avoid other end artifacts such as: fluctuation of the baseline temperature in the pulmonary artery caused by respiration, and significant loss of indicator in patients with pulmonary congestion, which may result in falsely high measurements.

The particular features and advantages of the present invention can best be appreciated from a detailed understanding of the system as described in the following detailed disclosure accompanied by the attached drawing wherein identical reference numerals will refer to like parts in the various views.

THE DRAWING

FIG. 1 is a functional block diagram of a system for computing cardiac flow rates incorporating the present invention;

FIG. 2 is an idealized graph showing a typical thermodilution curve from which blood flow rate is measured by the present system;

FIG. 3 is a frontal view of a cabinet housing the electronic circuitry and showing the various controls and indicators;

FIG. 8 is an idealized graph showing the timing for operation of the analog-to-digital converter; and FIG. 9 is a circuit schematic diagram showing a circuit for isolating the output of the automatic base line circuit for recording the thermodilution curve.

DETAILED DESCRIPTION

Figure 4:
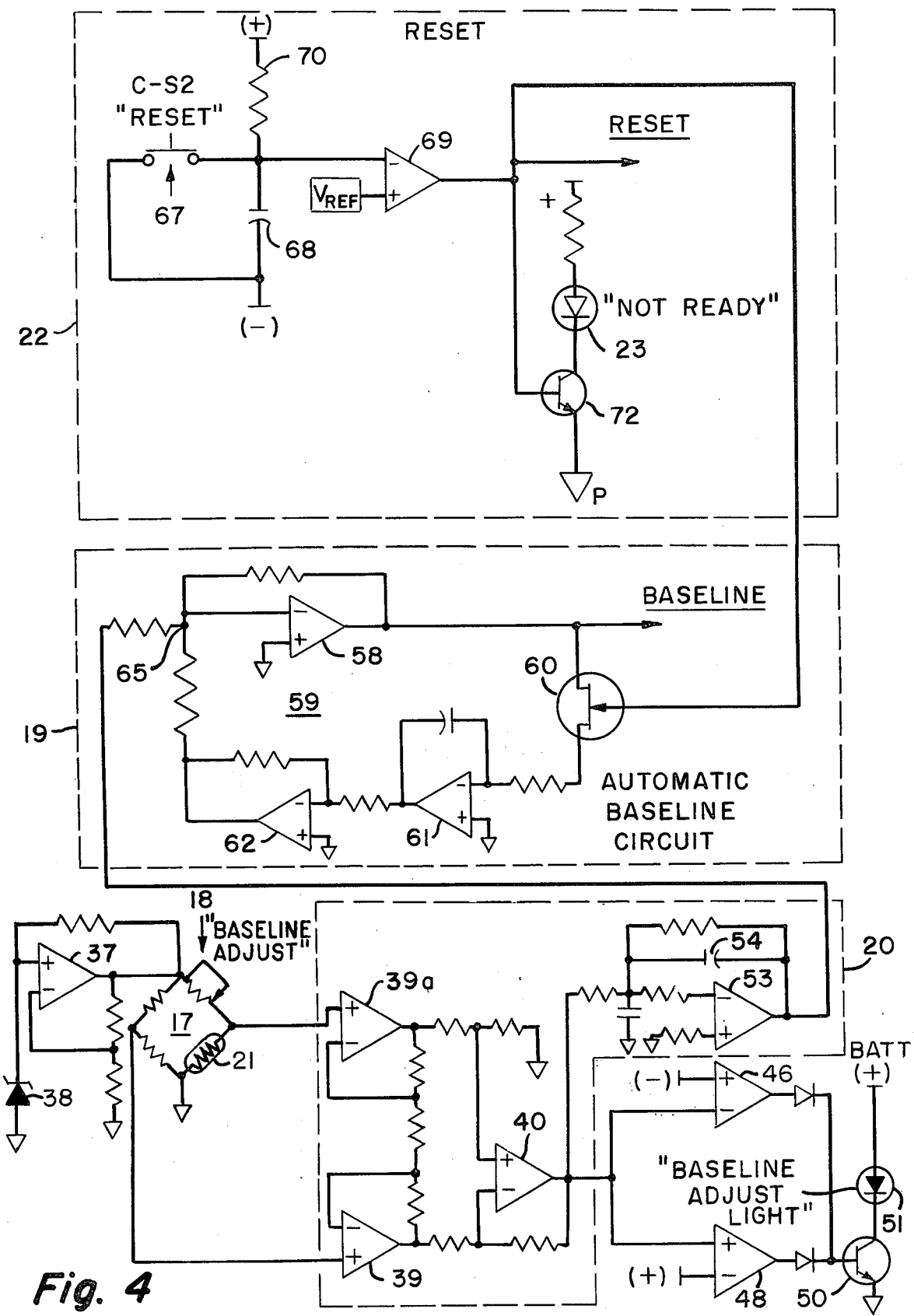
FIG. 4 is a more detailed logic schematic diagram of a portion of FIG. 1 showing the thermistor bridge, signal conditioning circuitry, automatic base line circuit, and reset circuit.

A better understanding of the detailed circuitry of the present invention will be obtained if first there is an understanding of the functions of the individual circuits as well as the overall system. Hence, a more generalized description of the system and its operation will be given prior to explaining the particular circuitry for accomplishing the functions.

Overall System

Referring first to FIG. 1, values for body temperature, injectate or indicator temperature, and computation constant are directly entered into the system by an operator using three sets of thumbwheel switches, generally designated respectively by reference numerals 10, 11 and 12. Each of the three sets 10, 11 and 12, in turn, includes three individual thumbwheel switches. The individual switches, for example, for the set 10 are designated 10A, 10B, and 10C.

Body temperature is determined by taking the temperature of the subject, either orally or rectally. Injectate temperature is determined directly, using a sterile mercury or electronic thermometer. Computation constant values are selected from a table, to be described presently. As indicated, the three values are designated respectively $T_B$, $T_I$ and K. These designations correspond to those used in Equation (1).

Table I gives the computation constants to be dialed into the system by the user, as a function of injectate temperature and volume, and the particular catheter being used. The catheter model numbers given in the table are the model numbers of catheters manufactured by Edwards Laboratories of Santa Ana, California, which are commercially available.

TABLE I

| | | Computation Constants | |
|---|---|---|---|
| | | Catheter Models | |
| Injectate Temp °C | Injectate Volume ML | 93-122-7F & 93A-118-7F | 93-120-6F & 93-121-6F |
| Iced (0–5° C) | 10 | .536 | .576 |
| | 5 | .242 | .272 |
| | 3 | .142 | .153 |
| Room (22–26° C) | 10 | .588 | .618 |
| | 5 | .286 | .302 |
| | 3 | .157 | .177 |

Computation constants not given in Table I may be computed from the first four terms of Equation (1), provided the correction factor $C_T$ for the temperature rise of the injectate as it passes through the particular catheter being used, is known.

The sets of thumbwheels 10, 11 and 12 may be seen in their physical arrangement in FIG. 3 which illustrates a frontal view of a cabinet for the computing system. The physical arrangements are designated respectively 10D, 11D, and 12D.

Each of the thumbwheels for the sets 10, 11 and 12 includes corresponding resistive values which are weighted according to the numeral appearing on the face of the dial as it turns, to generate a signal which is representative of the value appearing on the face of the dial.

The signals from the thumbwheel sets 10 and 11 are fed to a subtraction circuit 14, the output of which is fed to one input of a multiplication circuit 15. The other input of the multiplication circuit is received from the set of thumbwheels 12. The output signal of the multiplication circuit 15 is therefore representative of the quantity $[T_B - T_I]$ K, which signal is coupled to one input of a dual-slope, ratiometric analog-to-digital converter which is illustrated by the block 16.

The thermistor in the catheter is connected in an electrical bridge circuit which includes a balance adjustment 18. The corresponding balance adjusting knob is designated 18A on the front panel of FIG. 3. This provides a course null adjustment in the thermistor bridge circuit. Base line zeroing is then accomplished in an automatic base line circuit 19, after the output signal of the bridge 17 passes through signal conditioning circuitry 20, which principally amplifies and filters the output signal of the bridge 17.

The thermistor itself is illustrated at 21, and as mentioned, it is connected in circuit with the bridge 17 such that the output signal of the bridge circuit, designated $\Delta T_B(t)$, is a signal representative of the change in blood temperature as the indicator is injected.

Preferably, the catheter carrying the thermistor is positioned in the pulmonary artery of the subject, and after a preliminary check on the continuity of the thermistor 21, the base line adjust control 18 is used to null the thermistor bridge. Next, a Reset Button (designated 22A in FIG. 3) is depressed to actuate a reset circuit 22 in FIG. 1. The reset circuit 22 generates a signal for electronically zeroing the automatic base line circuit 19, and it also clears the digital circuitry and resets various circuits, as will be more fully discussed below. During the reset time, a "Not Ready" indicator light 23A on the front panel of FIG. 3 is illuminated for a period of about five seconds. When the indicator light 23A goes out, the base line is set, and the computing system is ready for a measurement cycle.

Immediately after the Not Ready indicator 23A goes out, the thermal indicator is injected as rapidly as possible (less than two seconds per five milliliters of injectate).

The thermistor 21 will sense the resulting change in blood temperature, and generate a signal representative of the resulting change in temperature as a function of time, similar to that shown in FIG. 2 and on Line 1A of the timing diagram of FIG. 8. This relationship is sometimes referred to as the "thermodilution curve".

Still referring to FIG. 2, reference numeral 24 indicates an exaggerated base line signal prior to reset, which occurs at time $T_O$ (the abscissa of the graph being representative of time). $T_R$ is the end of the reset period which is signaled when the indicator 23A turns off. $T_S$ is the start of the test cycle—that is, at the beginning of the injection of the indicator. Reference numeral 25, then, indicates the output signal of the automatic base line circuit 19, rising to a peak voltage $V_P$ and then declining along a curve which is generally similar to an exponential decrease.

The output of the automatic base line circuit is coupled to an integrator circuit 27 and to an automatic cutoff circuit 28. The integrator circuit 27, of course, integrates the input signal, and feeds it to a Sample and Hold Circuit 29. The integration is terminated by the automatic cutoff circuit 28 at a time when the thermodilution curve 25 has declined to 30 per cent of the peak voltage, indicated by the time $T_C$ of FIG. 2. The Sample and Hold Circuit 29 thus stores an analog signal representative of the integral of the curve 25 from its initiation up until the time $T_C$ of FIG. 2.

It will be recalled that tests have shown that the resulting value for the truncated interval (ending as it does at the time $T_C$), must be increased by 22% of the truncated integral value to establish an estimated integral value, which is representative of the integral of the entire area beneath the curve 25. This increasing of the truncated integral value may be done in any number of ways, but very simply, the amplifier in the integrator circuit 27 may have its gain increased to 1.22 over unity gain. In this case, the value of the truncated integral actually stored in the Sample and Hold Circuit 29 is in fact the estimated integral value.

The output signal of the Sample and Hold Circuit 29 is placed in the "hold" mode (that is, stored), by the automatic cutoff circuit 28 at the time $T_C$, and this signal is fed to the second input of the dual-slope, ratiometric analog-to-digital converter 16 is representative of the numerator of Equation (1) and the lower input is representative of the denominator of Equation (1).

The analog-to-digital converter 16 computes the ratio of the two input signals and generates a digital signal representative of the computation and which drives a display 33, comprising conventional seven-segment display elements using light-emitting diodes. The location of the display on the panel of FIG. 3 is shown at 33A, and there are three digit locations for displaying of blood flow rates up to 9.99 liters per minute. For flow rates measured greater than this value, the system will generate a flashing "8" on the most significant digit to display 33 to indicate an over-range condition. The range of the system may be extended to flow rates greater than 10liters per minute, as will be described below.

Thermistor Bridge and Signal Conditioning Circuitry

Referring now to the lower portion of FIG. 4, the thermistor 21 is connected as one branch of a bridge circuit 17 by means of a shielded catheter extension cable 36. The bridge circuit 17 is powered by an amplifier 37, the input signal of which is derived from a reference Zener diode 38. The coarse adjust resistor 18 may simply be a variable resistor or potentiometer, as shown, connected in the bridge circuit 17. Control, as mentioned, is achieved by means of the dial 18A on the panel of FIG. 3.

The output of the bridge circuit 17 is coupled to an input amplifier section including three individual differential amplifiers designated 38, 39 and 40, forming an instrumentation amplifier. The gain of this amplifier section is increased by 22% over what it normally would have been. The reasons for this will become apparent from subsequent description.

The output of amplifier 40 is connected to the negative input of a differential amplifier 46, to the positive input of a similar amplifier 48. The positive input of the amplifier 46 is referenced to a negative potential, and the negative input of the amplifier 48 is referenced to a positive potential. The amplifiers 46, 48 are connected in a circuit configuration known as a "window comparator" and serve as a "near" null detector and continuity detector for the catheter. If the output signal of amplifier 40 deviates from the null condition within the limits defined by the window, one of the amplifiers 46, 48 will generate a positive output and cause a transistor 50 to conduct, thereby illuminating a light-emitting diode 51 to signal the need for a "base line adjust" to the operator, the corresponding indicator lamp being designated 51A on the panel of FIG. 3.

The second important function of the window detector, as mentioned, is to indicate to the operator whether the catheter has a continuity fault or is operative. The light-emitting diode can be turned off by adjusting the baseline resistor 18 in the bridge 17 only when the resistance value of the thermistor branch of the bridge is within an acceptable range which, of course, is not the case if one of the lead wires to the thermistor is broken or becomes disconnected.

If the bridge is within the limits of the null region, the output signals of amplifiers 46, 48 will both be relatively low, and the diode 51 will not be energized.

The output of amplifier 40 is also connected to an amplifier 53 forming an active low pass filter in the circuit configuration illustrated for attenuating frequencies above 10 Hz.

Automatic Baseline Circuit

Still referring to FIG. 4, and particularly the automatic baseline circuit enclosed within the line 19 on its associated circuitry, the output of the amplifier 53 of the signal conditioning circuitry 20 is coupled to the input of a unity gain summing amplifier 58, the output of which is the output of the automatic baseline circuit, or simply the baseline signal. The output of the amplifier 58 is connected through a feedback loop 59 to its input. The feedback loop 59 includes a field effect transistor 60, an integrator 61, and an inverting amplifier 62 connected in series. A capacitor 63 forms a charge storage element for the integrator.

The field effect transistor 60 is used to reset the automatic baseline circuit 19, and it receives its input from the reset circuit 22, to be described. The transistor 60 is normally in a non-conducting state in the absence of a reset signal.

During reset, when transistor 60 is conducting, the output signal of amplifier 58 is coupled to the input of the integrator 61. The input of the amplifier 58, namely the junction 65 is a summing junction. Hence, the output of amplifier 58 is integrated and summed at the junction 65, continuously driving the output of the amplifier 58 toward zero since the amplifier 58 is connected in the inverting mode. When zero is reached, the integrator 61 no longer has an input voltage. Thus, its output remains constant, maintaining the output of amplifier 58 at zero. At the end of the reset time (nominally five seconds), transistor 60 becomes non-conducting, and the output of amplifier 61 holds the final value required to maintain the output of the amplifier 58, which is the output of the automatic baseline circuit at zero volts. Another way to look at the operation of the automatic baseline circuit is to suppose that a slight positive perturbation is present at the output during the reset period. This slight positive signal will be integrated by the amplifier 61 and applied to the summing junction 65. Because the amplifier 58 is an inverting amplifier, the output will tend to be reduced. Should the polarity of the perturbation be reversed, so will the effect of the feedback voltage.

Reset Circuit

Turning now to the lower left-hand portion of FIG. 4, and particularly the circuitry enclosed within the line 22 representing the reset circuit, reset is initiated by depressing a push switch 67, which shorts out a capacitor 68, when it is closed. The voltage across the capacitor 68 is fed to a comparator amplifier 69, the other input of which is a reference voltage. The output of amplifier 69 comprises the reset signal which is coupled, among other places, to the gate of the transistor 60 in the feedback loop of the automatic baseline circuit 19, just described.

One terminal of the capacitor 68 is coupled to the negative terminal of the supply voltage, and the other terminal is connected through resistor 70 to the positive terminal of the supply voltage. When the switch 67 is closed, the input of the amplifier 69 is strongly unbalanced, driving the output to the positive supply level which provides the reset signal. After the switch 67 is released, the capacitor 68 begins to charge according to the time constant determined by resistor 70 and capacitor 68; and when it reaches a sufficiently positive voltage, the output of the amplifier 69 returns to a low voltage. As mentioned, the circuitry is designed so that the reset signal lasts approximately five seconds to insure that the circuitry being reset has settled.

The output of the amplifier 69 is also connected to the base of a transistor 72, the collector circuit of which is provided with a light-emitting diode 23 functioning as a not ready indicator, as seen at 23A on the panel of FIG. 3.

Integrator Circuit

Figure 5:
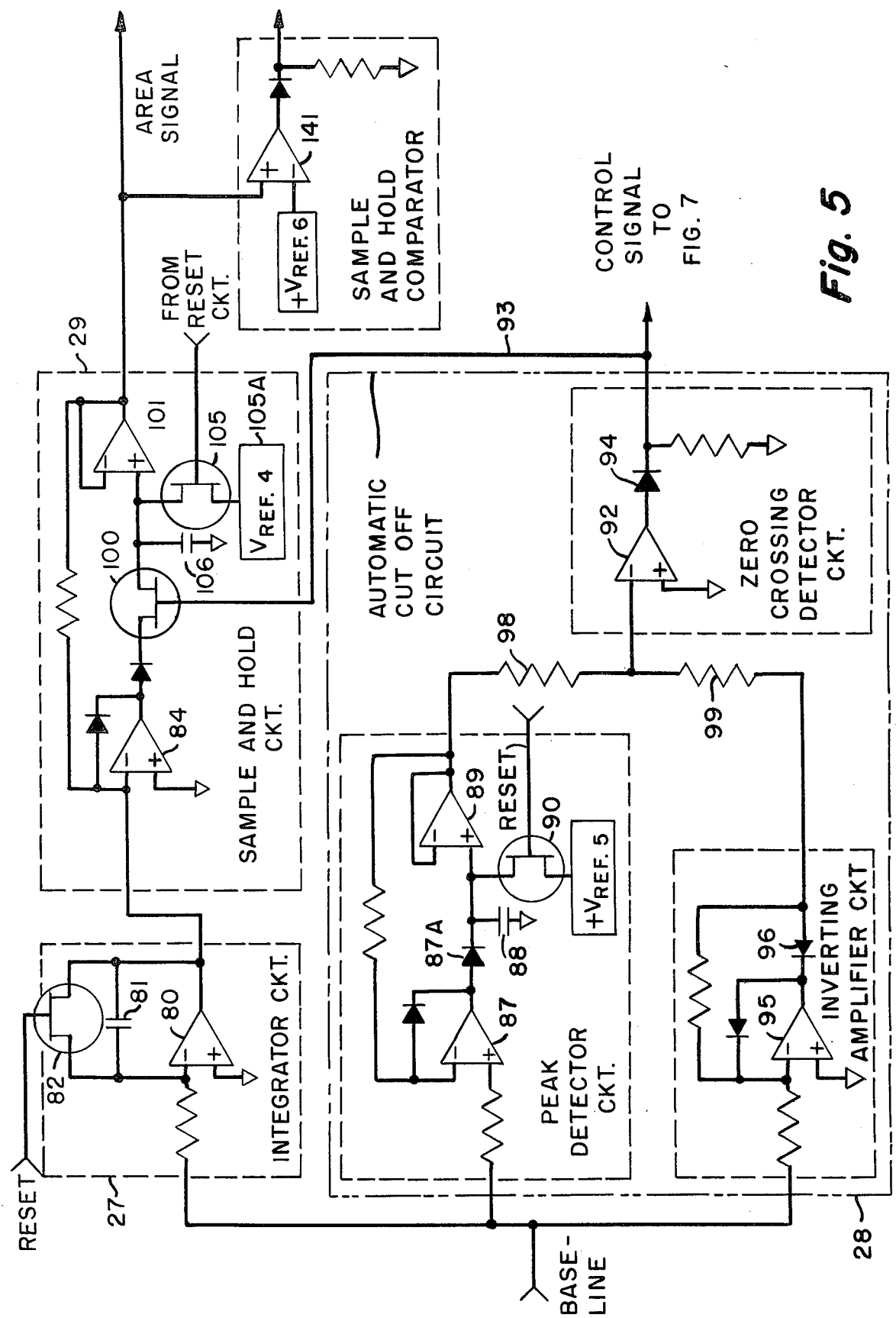
FIG. 5 is a more detailed circuit schematic diagram of a portion of the system of FIG. 1 showing the automatic cutoff circuit, integrator circuit and sample and hold circuit.

Referring now to FIG. 5, and particularly the circuitry enclosed within the dashed line 27, the integrator circuit includes an operational amplifier 80 having a capacitor 81 connected between its input and output terminals, and a field effect transistor 82 similarly connected. The gate terminal 83 of the transistor 82 is actuated by the previously described reset signal which, when present, causes the transistor 82 to conduct and thereby reset the integrator 27 by discharging capacitor 81. As mentioned, the input of the integrator circuit 27 is received from the output of the automatic baseline circuit 19 of FIG. 4; and its output is coupled to the input of the Sample and Hold Circuit, shown in FIG. 5 within the line 29.

Automatic Cutoff Circuit.

The automatic cutoff circuit, seen in FIG. 5 within the dashed line 28 also receives as its input, the output signal of the automatic baseline circuit 19; and it includes an amplifier 87, the output of which is coupled to a storage capacitor 88 and to the input of a second amplifier 89. A transistor 90 is connected across capacitor 88. The transistor 90 is actuated by the reset signal which, when present, causes the transistor 90 to conduct, thereby discharging capacitor 88.

The output of the amplifier 89 is coupled to the input of an inverting amplifier 92, the output of which is fed through a diode 94 to the Sample and Hold Circuit 29 and also forms a control signal, to be discussed.

The input of the automatic cutoff circuit is also connected to the input of an inverting amplifier 95, the output of which is coupled through a diode 96 to a summing junction at the input of the amplifier 92.

The amplifiers 87, 89 and the capacitor 88, connected in the illustrated configuration, form a peak detector circuit. That is, whatever positive charge has accumulated on the capacitor 88 will remain since the output of the amplifier 87 is isolated from it by means of a diode 87A. The capacitor 87 cannot discharge and retains its positive signal so that the output of the amplifier 89 remains at a level equal to the peak value of the input to amplifier 87.

During reset, transistor 90 is caused to conduct, discharging capacitor 88 and establishing a small positive voltage on the capacitor 88 which is reflected in the output of the amplifier 89. Amplifier 92 is a high gain inverting amplifier functioning as a zero crossing detector. Since the input to the automatic cutoff circuit is at zero volts at the termination of the reset period (since it is received from the automatic baseline circuit), the voltage at the junction between the two coupling resistors 98, 99 is slightly positive just before a thermodilution signal is presented to the system. This drives the output of amplifier 92 strongly negative; this output is applied to the Sample and Hold Circuit 29 and to the analog-to-digital circuitry, to be described (the latter being the control signal).

As the thermodilution signal is presented, the output of amplifier 95 immediately goes negative, while the output of amplifier 89 follows the rising thermodilution curve. As a result, the input of amplifier 92 is driven negative, causing its output to go strongly positive. This positive output voltage places the Sample and Hold Circuit in the "Sample" mode by causing a transistor 100 to conduct (thereby coupling the output of amplifier 84 to the input of an amplifier 101 in the Sample and Hold Circuit 29).

As the thermodilution signal reaches its peak and begins decaying, the peak voltage stored on capacitor 88 is held there and prevented from being discharged, as discussed above. When the curve falls below 30% of the peak value, the magnitude of the output signal from amplifier 95 falls below that of the magnitude of the output signal from amplifier 89, thereby switching the output of the zero crossing detector amplifier 92 and placing the Sample and Hold Circuit in its hold mode. In order to accomplish this result at the desired 30% of peak value, the gain of the amplifier 95 is set to be 3.33 times the gain of the peak detector circuit.

Further, in order to calculate the area under the entire thermodilution curve (i.e., to account for the area beneath the "tail" of the curve after integration is terminated), the value of the truncated integral is increased by 22%. In practice, this is accomplished by increasing the gain of the input amplifier section comprising amplifiers 38, 39 and 40 of FIG. 4 by 22%.

For example, in the illustrated embodiment, the gain of the input amplifier section is increased from a nominal gain of 100 to 122. The increase of the integral value by 22% is an estimate of the tail or remainder of the integral after cutoff. The particular percentage by which the value of the integral up to cutoff is increased depends, of course, upon when cutoff occurs. It has been found through statistical analysis of many thermodilution procedures that accurate results can be obtained by terminating the integration at 30% of the peak value (accomplished by the automatic cutoff circuit) and increasing the value of the integral by 22% (accomplished by the amplifier section). The early termination of the integration has the advantages of shortening the test time and avoiding the effects of artifacts which may occur thereafter.

In summary, the automatic cutoff circuit 28 generates an output signal which is positive as soon as a thermodilution signal is present, but which turns negative when the thermodilution curve reaches a predetermined fraction or per cent of the peak value on the decaying portion (in the present case, that predetermined percentage being 30% of the peak value, which is a preferred, but not necessary value).

Sample and Hold Circuit

As mentioned, the Sample and Hold Circuit 29 includes a field effect transistor 100 (FET) which is caused to conduct by the output signal of the automatic cutoff circuit 28. The FET 100 is connected in series with the input of a unity gain amplifier 101 connected in a follower configuration for high input impedance. The output signal of the amplifier 101 has a magnitude representative of the area beneath the thermodilution curve. The percentage by which the value of the integral will be increased will vary, depending upon the point at which the integration is cut off, but not as a function of recirculation of the indicator, as in the prior art patent referenced above.

An FET transistor 105 is connected in series with a reference voltage source 105A across a capacitor 106 which is connected between the signal input of amplifier 101 and the analog ground. The FET 105 is controlled by the reset signal.

The Sample and Hold Circuit 29 is cleared by the reset pulse—that is, the reset signal causes the transistor 105 to conduct, thereby coupling capacitor 106 to the reference voltage 105A to establish a small positive charge on the capacitor. During the reset period, as already discussed, the output of the automatic cutoff circuit is negative, and the FET transistor 100 is in a non-conducting state. When the FET transistor 105 conducts during reset, the slight positive charge just mentioned is established on the capacitor 106. The purpose of this charge will be discussed later.

When the thermodilution signal begins, the output of the automatic cutoff circuit goes positive, and the transistor 100 conducts, thereby coupling the output of amplifier 84 to the junction between the storage capacitor 106 and the input of amplifier 101.

When the transistor 100 conducts, the Sample and Hold Circuit is placed in the Sample mode, accumulating a voltage on the capacitor 106 which is representative of the peak output voltage of the integrator circuit. The voltage on capacitor 106 is, of course, immediately reflected at the output of the amplifier 101, generating the signal representative of the area under the thermodilution curve. When the integration is to be terminated, the output of the automatic cutoff circuit goes negative, as discussed, thereby causing transistor 100 to turn off and locking a voltage on capacitor 106 representative of the truncated integral value where it is held for further processing. This value, of course, is representative of the entire area under the thermodilution curve due to the increased gain of amplifier 84 in the Sample and Hold Circuit.

Temperature and Calculation Constant Circuits

Figure 6:
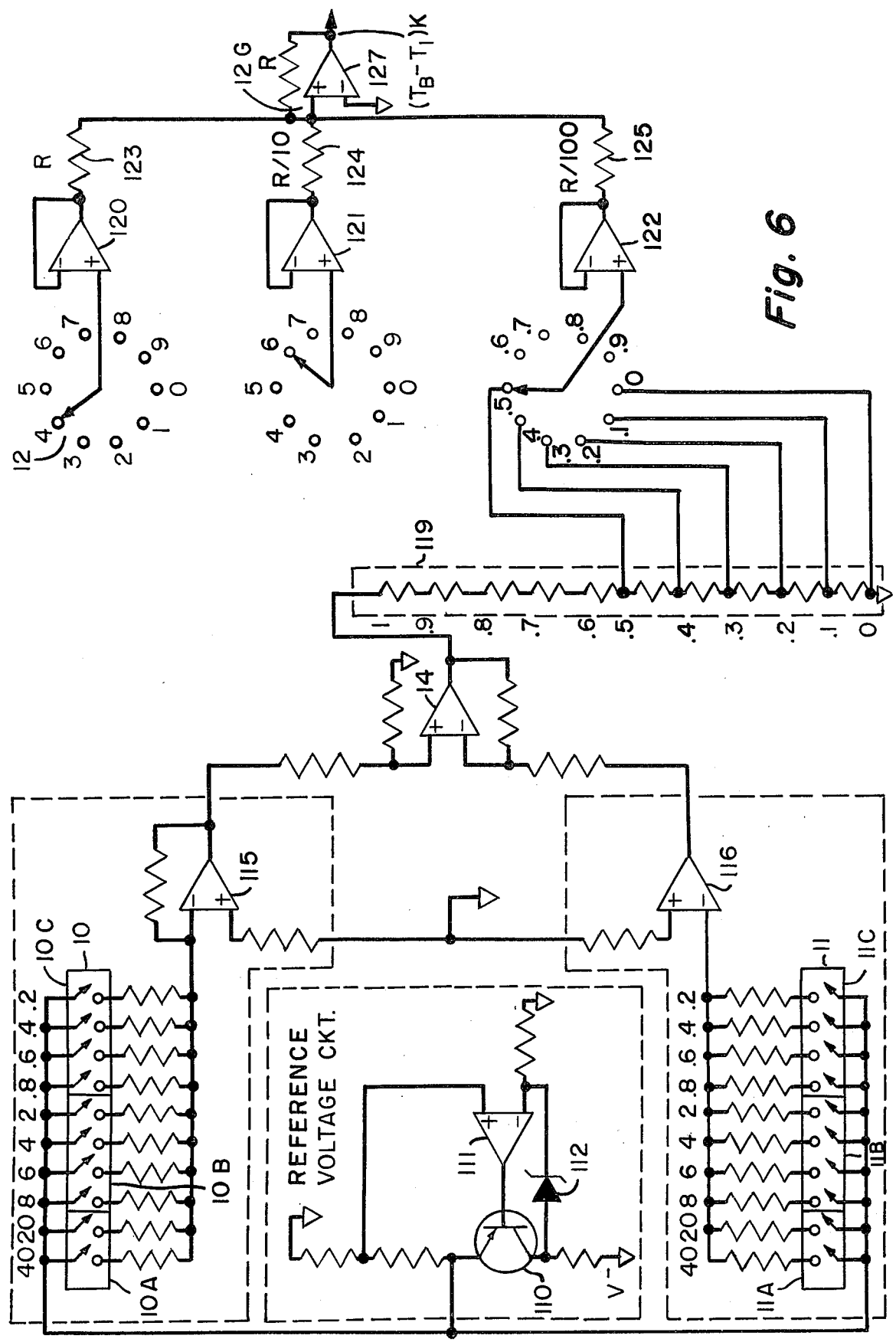
FIG. 6 is a more detailed circuit schematic of a portion of the system of FIG. 1 showing the generation of the signals representative of body temperature, indicator temperature, and computation constant.

Referring now to FIG. 6, there is shown a more detailed circuit schematic diagram of the temperature and calculation constant circuit. A reference voltage is generated by the circuitry comprising transistor 110, amplifier 111, and reference Zener diode 112, connected in the illustrated configuration. This voltage is applied to the sets of thumbwheel switches previously described, and indicated by reference numerals 10 and 11. Each set, as disclosed above, includes three separate thumbwheel switches, designated respectively 10A, 10B, 10C and 11A, 11B and 11C. The thumbwheels represent the decimal digits of the numbers being dialed into the system. The switches actuated by the thumbwheels select resistive values (relative values being indicated) according to the disposition of the associated thumbwheels for generating a signal representative of the number dialed. This signal is coupled to an amplifier 115 for the body temperature dialed, and to an amplifier 116 for the injectate temperature dialed.

The output signals of the amplifiers 115, 116 are connected respectively to the positive and negative terminals of the previously described subtraction circuit 14, which may be a differential amplifier, generating an output signal representative of the difference between the two input signals.

The output of the amplifier 14 is fed to a resistor network enclosed within the dashed line 119 (again, the relative values of resistance are indicated in the drawing). This network provides a voltage input for the set 12 of thumbwheel switches for the computation constants. Although only a portion of the connections are shown to the thumbwheel representative of the least significant digit, it will be appreciated that the same set of 10 lines couple the junctions of the network 119 to the terminals of the other thumbwheels. For the illustrated settings, the computation constant would be —0.465—. The resulting voltages selected the thumbwheel set 12 are applied respectively to buffer amplifiers 120, 121 and 122, each of which is provided with a scaling output resistor designated respectively 123, 124 and 125. These resistors are connected in common to form a summing junction 126 at the input of an amplifier 127, the output of which is a signal representative of the product $[T_B - T_I]$ K or "$\Delta T \times K$". The values of the scaling resistors 123–125 are such that resistor 124 is ten times greater than resistor 125, and the value of resistor 123 is 10 times greater than the value of resistor 124 so as to provide decade scaling.

In summary, then, the output of amplifier 127 is an analog signal, the magnitude of which is proportional to the computation constant times the quantity of the body temperature less the indicator temperature, as indicated in the output of the multiplication circuit 15 of FIG. 1.

Dual-Slope Ratiometric Analog-to-Digital Conversion and Display Circuits

Figure 7:
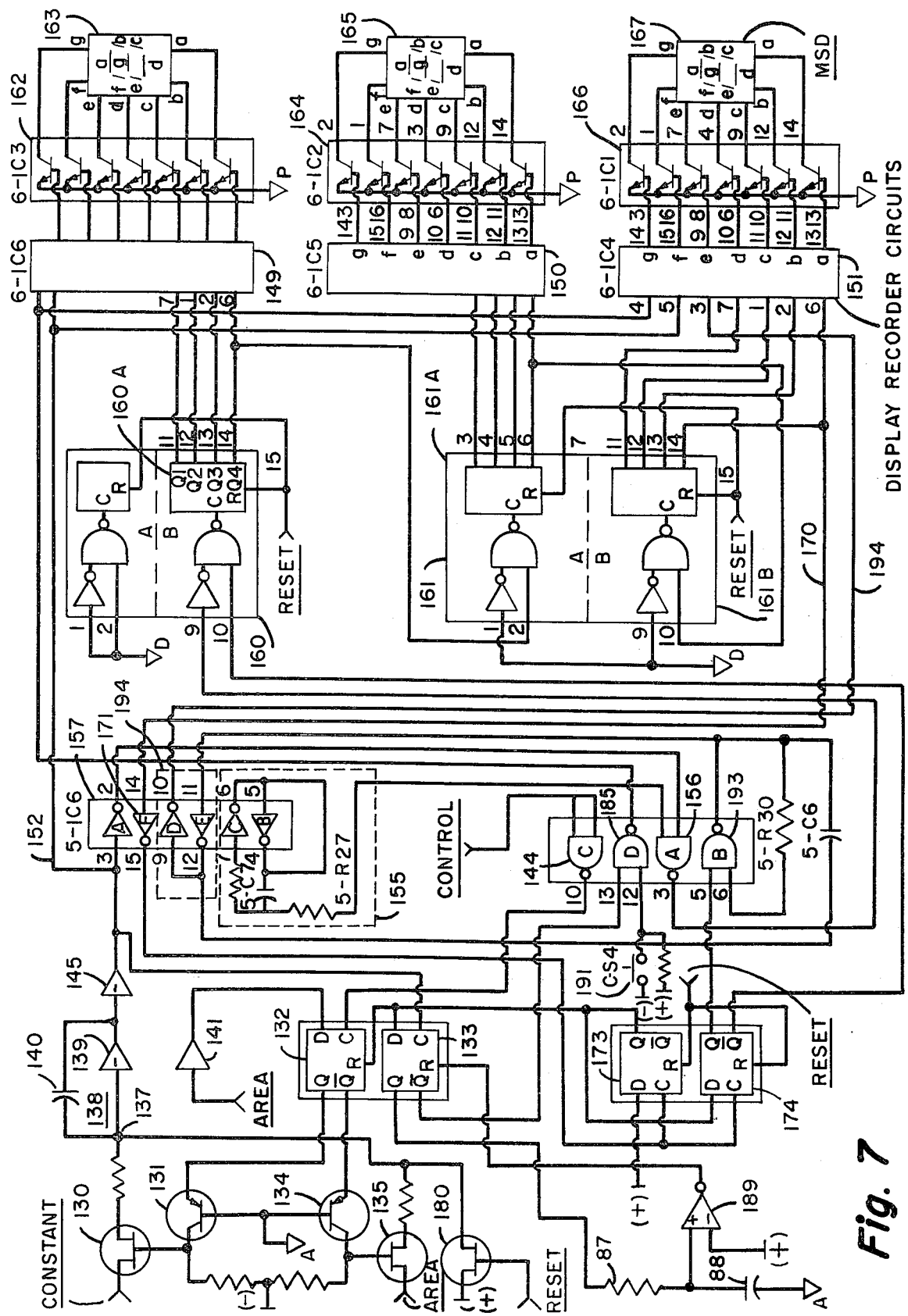
FIG. 7 is a detailed circuit schematic diagram of a portion of the system of FIG. 1 showing the analog-to-digital circuits, the display circuits, and the control circuits for the analog-to-digital converter.

Referring now to FIG. 7, a field effect transistor 130 is used as a switch for switching the signal from amplifier 127 of FIG. 6, just discussed, representative of the constant or numerator of Equation (1). The switching of transistor 130 is controlled by a second transistor 131, having its emitter connected to the Q output of a "D" type flip-flop 132.

As used herein, a D type flip-flop is one in which the signal level at the data or D input will be gated to the Q output on a positive-going signal at the clock or "C" input. The Circuit may alternatively be reset (i.e., "$\overline{Q}$" = 1) by a voltage level at the reset or "R" input. The $\overline{Q}$ is always the complement of the Q output.

In FIG. 7, certain of the solid blocks indicate the grouping of circuits as supplied by a manufacturer, for example, the flip-flop 132 is one of the pair, the other being designated 133; and its function will be discussed below.

The $\overline{Q}$ output of flip-flop 132 is connected to the emitter of the transistor 134 which controls the switching of a field effect transistor 135 for switching the output signal of the Sample and Hold Circuit 29 (specifically, the output signal of amplifier 101 of FIG. 5 which represents the estimated integral value for the area under the thermodilution curve). The switched signals from the transistors 130, 135 are connected to a summing junction 137 which is the input to an integrating circuit generally designated 138 and including an inverting amplifier 139 and a capacitor 140 connected in an integrator configuration. In summary, the circuitry just described receives the signal representative of the numerator of Equation (1) (the constant value) and the denominator of Equation (1) (the estimated integral value), and switches these values in mutually exclusive relation under control of the flip-flop 132 to the integrator 138. The $\Delta T \times K$ signal is negative in polarity.

The output of the integrator 138 as seen on line 4 of FIG. 8 is a positive ramp 142 followed by a negative ramp 143. The slope of each ramp is proportional to the magnitude of the corresponding input signal. That is, the slope of the positive ramp is proportional to the value of the $\Delta T \times K$ signal fed to the switching transistor 130, and the slope of the negative portion of the ramp 143 is proportional to the magnitude of the estimated integral signal fed to the switching transistor 135, the switching being controlled, as mentioned, by the flip-flop 132 and the transistors 131, 134 respectively.

The D input of the flip-flop 132 is connected to the output of a comparator amplifier 141, seen both in FIG. 5 and FIG. 7. When the input voltage exceeds a predetermined reference, $V_{REF6}$, the comparator 141 will generate an output signal. Thus, the comparator monitors the level of the signal representative of the estimated integral of (i.e. the area beneath) the thermodilution curve (line 1A of FIG. 8), received from the Sample and Hold Circuit 29. The C input of the flip-flop 132 is controlled by an inverter circuit 144 which receives as its input the control signal from the zero crossing detector circuit 92 through diode 94 of the automatic cutoff circuit of FIG. 5. It will be recalled that this signal goes HIGH at the start of a test and LOW at the time $T_C$ for cutoff (see line 1 of FIG. 8).

The sequence of operation is: before a thermodilution curve is measured, the $\Delta T \times K$ value will appear at the switching transistor 130. When a thermodilution signal is presented to the integrator circuit 27 after the reset period, the output of the automatic cutoff circuit goes HIGH (because the amplifier 95 has a greater gain than the peak detector circuit). The resulting control signal (see line 1 of FIG. 8) is coupled to the inverter 144 of FIG. 7. The flip-flop 132 is set on a negative-going voltage. When the area output from the Sample and Hold Circuit 29 increases during integration of the thermodilution signal, it causes the output of amplifier 141 of FIG. 7 to go HIGH (see line 2 of FIG. 8). When integration has taken place through such time as the thermodilution signal decays to 30% of its peak value, as discussed above, the output signal of the Automatic Cutoff Circuit 28 again goes LOW (see time $T_C$ of line 1, FIG. 8), which drives the Q output of flip-flop 132 HIGH, see line 3 of FIG. 3. The Q output of flip-flop 132 then causes transistors 131 and 130 to conduct, thereby presenting a signal to the integrator 138 which is representative of and proportional to the magnitude of the constant value. The output signal of the integrator, as previously discussed, is shown on line 4.

The output signal of the integrator is coupled to the negative terminal of a comparator circuit 145, the positive input of which is coupled to ground or zero volts. Hence, the output of the comparator 145, as seen on line 5 of FIG. 8 is HIGH when the output of the integrator 138 is less than zero volts. When the output of the integrator 138 crosses zero and becomes positive, the output of the comparator 145 changes state and becomes LOW, as at 147 in FIG. 8.

The output of the comparator circuit 145 generates a signal for enabling a gate circuit to transmit an oscillator or clock pulse into a counter for accumulation. It also enables three display decoder circuits (designated respectively 149, 150 and 151 in FIG. 7) by transmitting a positive-going pulse along line 152. This pulse is coupled to the LATCH ENABLE inputs of the display decoder circuits which are commercially available. Thirdly, the comparator 145, when it goes LOW, sets the flip-flop 133, the function of which is to disable the displays, as will be discussed.

The circuitry enclosed within the dashed line 155 forms a clock pulse generator, the output of which is coupled to one input of an NAND gate 156. The other input of the NAND gate 156 is received from the output of an inverter 157 which, in turn, is driven by the output of the comparator 145. Thus, when the output of the comparator 145 goes LOW, clock pulses are permitted to pass through the gate 156 and to the input of a first dual decade counter 160. A second dual decade counter is designated 161. For the three-digit readout illustrated, only three of the four decade counters are used. The first decade counter 160A drives the display decoder circuit 149 which, in turn, through a set of driver circuits 162 energizes a first display element 163 comprising the least significant digit of a display element 33A of the panel of FIG. 3. Similarly, the display decoder circuits 150 feed driver circuits 164 which, in turn, energize a display element 165 comprising the second most significant digit of the display, and the display decoder circuits 151 feed driver circuits 166 which energize a display element 167 comprising the most significant digit of the display. The display decoder circuits 150 are actuated by a first decade counter 161A of the dual decade counter 161, and the display decoder circuits 151 are energized by a second decade counter 161B thereof. Thus, the decade counters 160A, 161A and 161B are connected in such a manner as to count 1,000 incoming pulses from the clock circuit 155. When the first 1,000 pulses are counted, (see line 6 of FIG. 8), an overflow signal is generated on line 170 and coupled through an inverter 171 to the C inputs of two D-type flip-flops 173, 174 which are connected to form a shift register. This signal advances the shift register and resets the counter.

The Q output of flip-flop 173 is connected to the D input of flip-flop 174, the D input of flip-flop 133 and the reset input of flip-flop 132. Thus, this first over-flow pulse resets the flip-flop 132, thereby changing its output states and coupling the signal present at the switch 135 to the input of the integrator 138. Thereafter, the integrator proceeds along a negative slope, as indicated at 143 on line 4 of FIG. 8. As mentioned, the output ramp of the integrator 138 has a slope proprotional to its input. In summary, then, the output is allowed to ramp up for the duration of 1,000 clock pulses which are accumulated in the counter circuits. When the counter overflows at the count of 1,000, the input to the integrator is switched to the positive output of the Sample and Hold Circuit 29, and the integrator begins a negative ramp. Again, clock pulses are accumulated until the output of the integrator crosses zero, going in the negative direction. In doing so, it crosses the zero volt line a second time, and when this happens, the output of comparator circuit 145 changes back to HIGH, as indicated at line 5 of FIG. 8. This results in disabling the transmission of clock pulses to the counter circuits and it removes the LATCH ENABLE and the blanking signals from the display circuits 149, 150 and 151 in order to display the contents of the decade counters 160A, 161A and 161B. This number represents the ratio of the computation constant multiplied by the temperature difference to the area under the thermodilution curve (that is, the estimated integral value). It is known and can easily be demonstrated that where the slope of an integrator is proportional to the magnitude of its input voltage, and periodic pulses are accumulated for each of a positive and negative slope, the ratio of the number of pulses accumulated is proportional to the ratio of the voltages. In the present system, where the number of pulses for one ramp is constant at 1,000, the number of pulses accumulated for the second ramp is proportional to the ratio of the two voltages. If the number of counts during the negative ramp exceeds 1,000 before the integrator output crosses zero, an over-range indication is displayed, as will be discussed.

During the reset period, the reset pulse from the reset circuit 22 resets both flip-flops 173, 174 (that is, their Q outputs are low), and it clears the dual decade counters 160, 161. At the same time, the reset pulse is used to cause a transistor switch 180 to conduct; and this couples a fixed positive voltage to the input of the integrator 138, causing its output to be clamped at a negative level, as seen on line 4 of FIG. 8, even though the output of the integrator circuit 138 should be at this negative level after each measurement. This initial condition is assured by the switch 180.

After the first 1,000 pulses have been counted in the counter circuits, the overflow signal, as mentioned, is inverted by the inverter 171 and applied as the clock input of the flip-flops 173, 174 which are connected in a shift register configuration. The data input of flip-flop 173 is connected to a positive level, so that when the clock pulse appears (at the occurrence of the first 1,000th pulse), a "1" is transferred to the Q output of flip-flop 173. Since the Q output of flip-flop 173 was previously LOW, no output change occurs in flip-flop 174 at this time. However, the high level at the Q output of flip-flop 173 is transmitted to the data inputs of flip-flops 174 and 133, and to the reset input of flip-flop 132. The transition from a LOW level to a HIGH level resets flip-flop 132, as seen at line 7 of FIG. 8, thereby causing switch 135 to conduct and applying the voltage representative of the estimated integral value to the input of the integrator 138. As a result, the integrator begins its negative ramp at a rate proportional to the magnitude of the estimated integral value (representing the total area beneath the thermodilution curve). During this time, the Clock Enable Gate 156 remains in an enabled state so that clock pulses continue to be accumulated in the three operative decade counters.

When the output of the integrator 138 crosses zero in the negative direction, the output of the comparator 145 changes to a high state, again referring to line 5 of FIG. 8. This signal disables the Clock Enable Gate 156 and terminates the transmission of clock pulses to the counter circuits. The HIGH output of the comparator circuit 145 also disables the latches in the display decoder circuits 149, 150 and 151, thereby storing the final count appearing in the counters. The LOW to HIGH transition of the comparator 145 is also applied to the clock input of flip-flop 133, and this causes the HIGH data input level to be transferred to the Q output. The resulting LOW state of the $\overline{Q}$ output enables a NAND gate 185 which, in turn, feeds a signal to the display decoder circuits enabling the input signals to be transmitted to the drivers and thereby energize the displays 163, 165 and 167.

The HIGH level at the Q output of flip-flop 133 is applied to an RC network, comprising resistor 187 and capacitor 188. When the voltage on the capacitor 188 becomes greater than a predetermined fixed voltage at the inverting input of a comparator circuit 189, its output changes to reset flip-flop 133. Thus, the circuitry just described comprises a time delay for resetting the flip-flop 133 so that its output appears as a pulse, as seen on line 9 of FIG. 8. It is this signal which enables the display of the contents of the registers. The gate 185 may also be enabled by actuating a switch 191, the actuator for which is located at 191A on the panel of FIG. 3. This enables the operator to redisplay a count stored in the display decoder circuits 149, 150 and 151.

When the counter accumulates 1,000 clock pulses on the negative slope 143 before the output of the integrator circuit 138 crosses zero, an "overrange condition" results. The 1,000th pulse causes all counter outputs to reset to their LOW states (for the second time in this cycle). This transition of counter 161B generates a LOW-going pulse on line 170 which is inverted by the inverter 171 and applied to the clock inputs of flip-flops 173, 174. As a result, the HIGH levels at the data inputs of flip-flops 173, 174 are transferred to the Q outputs. It will be observed that since the Q output of flip-flop 173 was previously HIGH, no change in its output occurs. The HIGH level at the Q output of flip-flop 174 enables a NAND gate 193, the other input of which is the output of an oscillator circuit comprising the active elements within the dashed line 194 and the associated capacitor and resistor seen in circuit with them. The output of the oscillator, when the gate 193 is enabled is a signal transmitted along line 194 to the lamp test input of display decoder circuit 151 which results in a flashing numeral 8 at the most significant digit element 167 of the display. The low level at the Q output of flip-flop 174 inhibits the counter from accumulating any more pulses.

Referring to FIG. 8, when an "overrange condition" occurs, as represented by the dashed negative slope 143A in line 4, the output of the inverter circuit 145 (line 5) does not return to its HIGH state until after 1,000 pulses have occurred (line 6). As just discussed, the second occurrence of the 1,000th pulse causes the Q output of the flip-flop 174 to go HIGH, as seen by the dashed signal level in line 8 of FIG. 8 for causing the flashing numeral 8 in the most significant digit, and delaying the overrange pulse as seen on line 9 of FIG. 8 to the dashed position.

If it is desired to extend the range of the system above 9.99 liters per minute, the computation constant for a given volume of indicator may be divided by two, prior to entering into the set of thumbwheel switches 10. The actual cardiac output flow rate is then calculated by multiplying the rate displayed by the system by a factor of 2. Factors other than 2 may be used obviously.

To extend the measuring range below the lower range limit, the volume of the injectate must be reduced or its temperature must be increased and the appropriate computation constant must be entered.

Isolation Circuit

When it is desired to record the actual curve of the thermodilution signal of FIG. 2, the isolation circuit of FIG. 9 may be used to completely isolate the measuring electronics from the recording electrical system. Referring then to FIG. 9, the output signal of the Automatic Baseline Circuit 19 is coupled directly to amplifier 210 which drives the diodes 211 and 212 connected in series, each diode belonging to a light-emitting diode-phototransistor pair, generally designated respectively 213 and 214. A feedback path is provided from the light-emitting diode 211 to the input of the amplifier 210 by the transistor 213 to linearize the circuit, the optical isolation being provided by the pair 212, 214, the output of which is coupled through an amplifier 217 to a recording jack 218.

There is also provided a pushbutton 219 connected between the input to the amplifier 210 and the positive voltage source. When the switch 219 is closed, a reference level is applied to the input of the amplifier 210, and this input voltage is reflected in the isolated output as a 1° C. level (1 volt) for calibration of the recorded curve. The actuator for the switch 219 is shown at 219A on the panel, FIG. 3.

Referring then to FIG. 3, reference numeral 218A indicates the physical location of the recorder jack on the panel. Reference numeral 225 indicates a receptacle for the extension cable for the thermodilution catheter. the recorder jack 218A and socket 225 are located in a recess 226 and may be covered by a sliding door 227 when the system batteries are being charged. Thus, behind the door 227 is an alternating current receptacle 228 which accepts a charging cord. The system is operated on batteries of low voltage (nominally 10.5 to 13.5 volts DC) so as to avoid any possibility of shock hazard during use. The batteries may be charged either on 115 volts AC or 230 volts AC, depending upon the position of the selector switch 230 and the available power.

Reference numeral 231 indicates the location of a fuseholder and fuse for protecting the battery charger, and reference numeral 232 indicates a similar fuseholder and fuse to protect the power supply.

A main power switch is provided at 233 for selecting one of three modes, including OFF for periods of non-use, ON for normal operation, and CHARGE for charging the batteries. During charging of the batteries, an indicator lamp 235 is lit relatively brightly, and turns to a dimmer illumination when the battery is fully charged. If the batteries are low, an indicator lamp 235 is illuminated, indicating to the operator that the lower limit of battery operation will be reached in less than 15 minutes of use. This lamp is flashed when the system can no longer be used. The circuitry for performing the charging and indicator operations just described are conventional and form no necessary part of the present invention.

Having thus described in detail one embodiment of the invention, persons skilled in the art will be able to modify certain of the circuitry which has been disclosed and to substitute equivalent elements for those illustrated while continuing to practice the principle of the invention; and it is, therefore, intended that all such modifications be covered as they are embraced within the spirit and scope of the appended claims.

I claim:

1. In a system for measuring blood flow rate by injecting a predetermined amount of indicator at a known initial temperature into the bloodstream and measuring the temperature of the blood at a location downstream of the point of injection, apparatus comprising: circuit means for generating a constant signal representative of the product of a computation constant times the quantity of the initial blood temperature minus the initial indicator temperature; means sensing the temperature of the blood downstream of the location of injection of said indicator for generating a thermodilution signal representative of the combined temperature of the blood and indicator; means responsive to said thermodilution signal for generating a signal representative of the integral of said thermodilution signal to a predetermined fraction of the peak value thereof on the decay portion of said thermodilution signal increased by a predetermined percentage, said signal being an estimated integral signal representative of the entire area beneath the thermodilution curve; dual-slope, ratiometric analog-to-digital converter means receiving said constant signal and said estimated integral signal for generating digital signals representative of the ratio of said constant signal to said estimated integral signal and including counter-circuit means for storing said digital signals; and display circuit means responsive to the output signals of said counter-circuit means for displaying visual indicia representative of the contents of said counter means, said visual signals being a measure of blood flow rate.

2. The apparatus of claim 1 wherein said circuit means for generating said signal representative of said estimated integral of the thermodilution curve comprises a first integrator circuit receiving said thermodilution signal for integrating the same; Sample and Hold Circuit means receiving the output signal of said integrator circuit means for storing a signal representative thereof and including a switching circuit switchable between a conducting state for receiving said signal from said integrator circuit means and a non-conducting state for inhibiting the reception of said output signal of said integrator circuit means; and automatic cutoff circuit means responsive to said integral signal for generating a signal to turn said switching circuit means of said Sample and Hold Circuit Means to a non-conducting state after said thermodilution signal has passed through a peak and reaches a predetermined fraction of said peak, thereby retaining a signal in said Sample and Hold Circuit Means representative of the integral of the thermodilution curve until the time said switching means becomes non-conducting.

3. The apparatus of claim 2 wherein said means responsive to said thermodilution signal includes amplifier means receiving said thermodilution signal for increasing the same by a predetermined percentage to generate said signal representative of the estimated area beneath the entire thermodilution curve.

4. The apparatus of claim 1 wherein said analog-to-digital converter means includes oscillator circuit means for generating a train of periodic pulses and including gating circuit means responsive to an enable signal for transmitting said pulses to an output; switching circuit means receiving said constant signal and said estimated integral signal for isolating the same and for switching one of said signals to an output exclusive of the other in response to an input signal, said constant signal and said estimated integral signal being of opposite polarities; second integrator circuit means receiving the output signal of said switching circuit means for integrating the same, thereby to generate a linear ramp signal proportional to the magnitude of the output signal of said switching circuit means; counter circuit means for accumulating pulses to generate digital signals representative of the accumulated pulses, said counter circuit means further generating an overflow signal when a predetermined number of pulses is counted; and control circuit means responsive to the output signal of said cutoff circuit to activate said switching circuit means to gate said constant signal to said integrator circuit and responsive to said overflow signal to switch the state of said switching circuit means to gate said estimated integral signal to said second integrator circuit means; said gating circuit means of said oscillator circuit means being actuated at the start of an integration period to gate the output pulses of said oscillator to said counter-circuit means, said counter-circuit means overflowing when said predetermined number of pulses is accumulated, whereby the count retained in said counter circuit means is representative of the ratio of said constant signal to said estimated area signal.

5. The apparatus of claim 4 further comprising flip-flop circuit means responsive to the presence of said estimated area signal of said integrator circuit means and wherein said automatic cutoff circuit includes a control output signal occurring at said cutoff time, said control output signal being coupled to said flip-flop circuit means, said flip-flop circuit means being connected in circuit with said switching circuit means of said analog-to-digital converter circuit means to switch said estimated area signal to said second integrator circuit means at said cutoff time.

6. The apparatus of claim 5 wherein said counter circuit means comprises a plurality of decade counters, one for each digit in order of significance of said flow rate, said overflow signal being generated when all of said decade counters have returned to zero; said analog-to-digital converter means further comprising shift register means responsive to the first overflow signal to change the state of said flip-flop circuit means to present said estimated area signal to said second integrator circuit and responsive to the second overflow signal of said decade counter circuits to actuate said display elements to display the indicia representative of the contents of said decade counters.

7. The apparatus of claim 6 wherein one of said decade counters and associated display element is representative of the most significant digit of said display and is responsive to said second overflow signal for flashing a predetermined symbol to communicate to the operator that the measurement is overrange.

8. The apparatus of claim 1 wherein said circuit for generating said constant signal comprises a plurality of thumbwheel switching circuits, one representative of a computation constant, one representative of the initial blood temperature, and one representative of the initial indicator temperature for generating signals representative of each, said system further comprising subtraction circuit means for subtracting said signal representative of initial indicator temperature of said signal representative of initial blood temperature to generate a constant temperature difference signal, said system further comprising multiplication circuit means for generating a signal representative of a product of a constant signal and said constant temperature difference signal, said output of said multiplication circuit comprising said constant signal.

9. The apparatus of claim 1 wherein said means for generating said thermodilution signal includes a bridge circuit incorporating said thermistor, one leg of said circuit including a variable resistor for approximate null adjustment, said system further comprising window comparator circuit means responsive to the output of said bridge for indicating when the null signal of said bridge exceeds a predetermined positive limit or is less than a predetermined negative level, for generating a visible signal in response thereto, said variable resistor for null adjustment being incapable of bringing the output signal of said window comparator circuit means within said limits when a circuit discontinuity exists in said thermistor bridge circuit.

10. The apparatus of claim 9 further comprising amplifier circuit means for receiving the output signal of said bridge for amplifying the same to increase the same by said predetermined percentage, and low-pass filter circuit means for filtering said output signal of said bridge.

11. The apparatus of claim 10 further comprising an automatic baseline circuit receiving the output signal of said filter circuit means for establishing an automatic baseline and including a first amplifier and a feedback amplifier loop including an integrator amplifier receiving the output signal of said first amplifier of said baseline circuit means and coupling the same to the input thereof.

12. The apparatus of claim 11 further comprising reset circuit means manually actuatable by an operator for generating a reset signal of predetermined time, said reset signal being operative to reset said automatic baseline circuit, said counter-circuits and said analog-to-digital converter circuit means.

* * * * *